United States Patent
Bille

(10) Patent No.: US 7,800,760 B2
(45) Date of Patent: Sep. 21, 2010

(54) SYSTEM AND METHOD FOR HIGH RESOLUTION IMAGING OF CELLULAR DETAIL IN THE RETINA

(75) Inventor: Josef F. Bille, Heidelberg (DE)

(73) Assignee: Heidelberg Engineering GmbH, Heidelberg (DE)

( * ) Notice: Subject to any disclaimer, the term of this patent is extended or adjusted under 35 U.S.C. 154(b) by 267 days.

(21) Appl. No.: 12/105,179

(22) Filed: Apr. 17, 2008

(65) Prior Publication Data
US 2009/0262360 A1    Oct. 22, 2009

(51) Int. Cl.
*G01B 11/02* (2006.01)
(52) U.S. Cl. ................ 356/497
(58) Field of Classification Search ............ 356/478, 356/497, 479, 477; 351/200, 205, 209, 210
See application file for complete search history.

(56) References Cited

U.S. PATENT DOCUMENTS

| | | | | |
|---|---|---|---|---|
| 4,579,430 A * | 4/1986 | Bille | ............ | 351/206 |
| 4,881,808 A | 11/1989 | Bille et al. | | |
| 5,920,373 A | 7/1999 | Bille | | |
| 5,943,133 A | 8/1999 | Zeylikovich et al. | | |
| 6,271,915 B1 * | 8/2001 | Frey et al. | ............ | 356/124 |
| 6,709,108 B2 * | 3/2004 | Levine et al. | ............ | 351/211 |
| 2003/0071969 A1 | 4/2003 | Levine et al. | | |
| 2004/0002694 A1 | 1/2004 | Pawlowski et al. | | |
| 2007/0103642 A1 | 5/2007 | Bille | | |
| 2007/0291277 A1 * | 12/2007 | Everett et al. | ............ | 356/497 |

OTHER PUBLICATIONS

Liang, et al., "Objective measurement of wave aberrations of the human eye with the use of a Hartmann-Shack wave-front sensor," Jul. 1994, J. Opt. Soc. Am. A, vol. 11, No. 7, pp. 1949-1957.*

* cited by examiner

*Primary Examiner*—Michael A Lyons
*Assistant Examiner*—Scott M Richey
(74) *Attorney, Agent, or Firm*—Neil K. Nydegger

(57) ABSTRACT

A system and method for imaging tissue cells at a predetermined depth in the retina of an eye include components that provide for compensation of refractive errors. Specifically, the system basically includes three subassemblies that operate in concert with each other. There is a first subassembly for directing a first light beam into the eye to measure anterior optical aberrations. There is also a second subassembly for directing a second light beam through retinal tissue to a predetermined depth where the tissue cells are located. This second light beam is used to measure phase aberrations introduced by the retinal tissue. And, there is a third subassembly for directing a third light beam to the tissue cell to produce an image of the tissue cell. In the third light beam, the anterior optical aberrations and the phase aberrations have been substantially removed to provide a clearer image of the tissue cell.

20 Claims, 2 Drawing Sheets

SYSTEM AND METHOD FOR HIGH RESOLUTION IMAGING OF CELLULAR DETAIL IN THE RETINA

FIELD OF THE INVENTION

The present invention pertains generally to systems and methods involving ophthalmic diagnostic equipment and their use for imaging tissue in the retina of an eye. More particularly, the present invention pertains to systems and methods for removing refractive errors from a light beam that is to be used for ultra-high-resolution of cell tissue in the retina. The present invention is particularly, but not exclusively, useful as a system and method for imaging tissue cells at a predetermined depth in the retina.

BACKGROUND OF THE INVENTION

Optical Coherence Tomography (OCT) is an imaging modality that is known to be efficacious for use in imaging retinal tissue. In general, OCT imaging is analogous to the more well-known technique of ultrasound imaging. Unlike ultrasound imaging, however, OCT imaging uses light instead of sound. Importantly, OCT imaging can be accomplished in situ, and in real time. Like almost every other optical measuring technique, in order to be effective, OCT imaging requires a useable signal-to-noise ratio (SNR). Stated differently, optical aberrations that may be introduced into an imaging light beam need to be eliminated or significantly reduced before the beam can be most effectively used for imaging.

The ability of a system to image an object will depend on the nature of the particular application and, most importantly, the physical characteristics of the imaging light beam. With this in mind, light returning from inside the eye can be generally categorized as being either backreflected (i.e. regular reflection of light), or backscattered (i.e. irregular reflection or dispersal of light). Importantly, these categories of light can be analyzed in different ways, for different purposes. And, depending on the purpose (i.e. application), backreflected and backscattered light can be evaluated differently in either the time domain or in the frequency domain.

In a time domain analysis, a beam of light that is backreflected from a target tissue can be evaluated using conventional wavefront analysis techniques. Also, in a time domain analysis, OCT techniques can be employed when an interferometer is used to identify the wavelengths of light that is backscattered from a target tissue. Typically, these time domain techniques will be accomplished using a Hartmann-Shack sensor. In these time domain analyses, evaluations can be performed to detect aberrations that are introduced into an imaging beam by the anatomical structures that are in its path. For example, it is known that anterior components of an eye (e.g. the cornea and lens) will introduce anterior optical aberrations into a light beam that passes through the components. Insofar as the retina is specifically concerned, it is also known that phase aberrations are introduced into a light beam as it passes through retinal tissue. Fortunately, these introduced aberrations can be measured.

In the Fourier domain (i.e. frequency domain), OCT techniques can again be used on backscattered light. This time, however, rather than using an interferometer and a Hartmann-Shack sensor for wavefront analysis as is done in a time domain analysis; in the Fourier domain, OCT techniques typically use a spectrometer that evaluates frequency distributions in the light beam. Further, instead of measuring aberrations, the purpose for using the OCT techniques in the Fourier domain involves imaging. As indicated above, this is preferably done with as high of an SNR as is possible.

In light of the above it is an object of the present invention to provide a system and method for imaging a tissue cell at a predetermined depth in the retina of an eye, with compensation for refractive errors. Another object of the present invention is to provide a system and method for imaging a retinal tissue cell wherein the signal-to-noise ratio (SNR) is sufficiently high to allow for ultra-high-resolution OCT. Still another object of the present invention is to provide a system and method for imaging retinal cell tissue that is easy to use, is simple to implement and is comparatively cost effective.

SUMMARY OF THE INVENTION

In accordance with the present invention, an optical imaging system for viewing cell tissue in the retina of an eye includes a subassembly for generating an imaging light beam. Also included in the system are subassemblies for removing refractive errors from the imaging light beam. Importantly, if not removed, these refractive errors would be introduced as anterior optical aberrations and phase aberrations that will degrade the imaging light beam. In this context, anterior optical aberrations are refractive errors introduced by anterior components of the eye (i.e. the cornea and the lens). On the other hand, phase aberrations are introduced by retinal tissue that lies between the light source of the imaging light beam and the cell tissue that is to be imaged.

As inferred above, the cell tissue that is to be imaged by the system of the present invention will typically be located within the retina. Furthermore, the particular cell that is to be imaged in the retina may have a largest dimension that is as small as about ten microns. Accordingly, in order to effectively image the cell, resolution of the imaging subassembly needs to be on the order of less than five microns and, preferably, around one micron.

For purposes of the present invention, the imaging subassembly has a light source (e.g. a super luminescence diode) for generating an imaging light beam that has a wavelength of approximately 800 nm. Further, it has a very broad bandwidth of approximately 200 nm. The imaging subassembly also includes a spectrometer for use in a Fourier domain OCT technique for analyzing light from the imaging light beam that has been reflected by the tissue cell that is to be imaged. With the Fourier domain OCT technique, and due to the very broad bandwidth of the imaging light beam, the imaging subassembly can achieve a resolution of less than about 5 microns.

As mentioned above, in order to achieve an effective resolution for the imaging subassembly, refractive errors need to be removed from the imaging light beam. This is done by other subassemblies in the system. Specifically, a first subassembly is used to remove anterior optical aberrations, and a second subassembly is used to remove phase aberrations.

A first subassembly measures refractive errors that can be categorized as so-called anterior optical aberrations. The light source for this first subassembly generates a light beam of approximately 488 nm and may be of any type well known in the pertinent art. This subassembly also includes a wavefront sensor (e.g. a Hartmann-Shack sensor) for use in measuring the wavefront that is caused by anterior optical aberrations. Preferably, the light that is used to measure these aberrations will be reflected form the foveal area of the retina (i.e. the fovea) where scattered light in the reflected light beam is minimized. In any event, these measurements can then be used to program an active mirror for the purpose of removing the anterior optical aberrations from the imaging light beam.

A second subassembly measures refractive errors that can be categorized as so-called phase aberrations. The light source in this second subassembly (e.g. another super luminescence diode) generates a light beam of 800 nm. Unlike the imaging light beam disclosed above, however, its bandwidth need be only about 30 nm. Importantly, the second subassembly uses its light beam in a time domain OCT technique. It also incorporates an interferometer for use with the time domain OCT technique to measure the phase aberrations introduced by retinal tissue. Specifically, these phase aberrations are collectively obtained from retinal tissue that extends from the surface of the retina to a predetermined depth in the retina. For the present invention, this predetermined depth is where the tissue cell(s) to be imaged is (are) located. Like the anterior optical aberrations disclosed above, the phase aberrations are measured and used to program an active mirror for the purpose of removing phase aberrations from the imaging light beam. As envisioned for the present invention, both the first and second subassemblies can employ the same active mirror. In either case, the imaging light beam is directed into the eye by an active mirror that is programmed to remove refractive errors.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
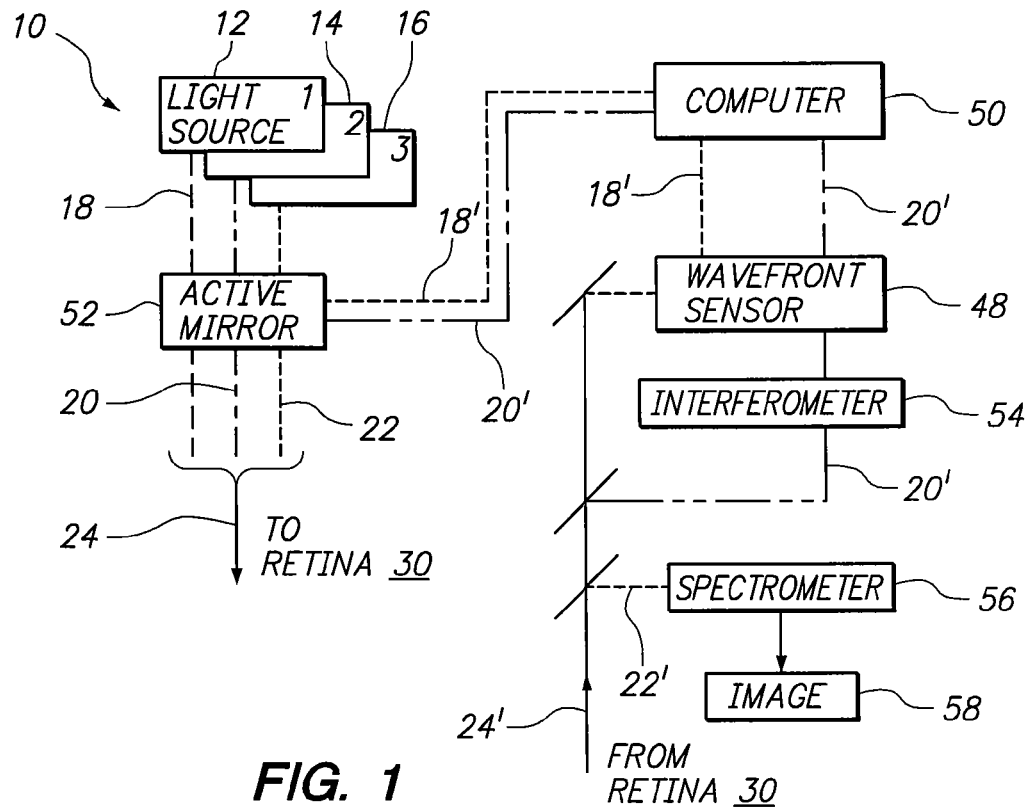
FIG. 1 is a schematic representation of the system of the present invention with subassemblies and associated components arranged for its operation.

Referring initially to FIG. 1, a system in accordance with the present invention is shown and is generally designated 10. As shown, the system 10 operationally includes three subassemblies that can be generally differentiated from each other by their respective light sources. Thus, a first subassembly has a light source 12. A second subassembly has a light source 14. And, a third subassembly has a light source 16. Respectively, these subassemblies (i.e. light sources 12, 14 and 16) generate a light beam 18 (represented by a dashed line), a light beam 20 (represented by a dot-dash line), and a light beam 22 (represented by a dotted line). The common beam path for these various light beams 18, 20 and 22 is numerically designated 24. Further, light traveling this beam path 24 may also be designated 24 and, as so used, may designate any of the various light beams 18, 20 or 22.

Each of the light sources 12, 14 and 16 in system 10 are substantially different from each other. In detail, the light source 12 of the first subassembly may be of any type well known in the pertinent art that will generate a light beam 18 (dashed line) having a wavelength of approximately 488 nm. On the other hand, the light source 14 for the second subassembly is preferably a superluminescent diode that generates a light beam 20 (dot-dash line) having a wavelength of approximately 800 nm. Further, this light beam 20 of the second subassembly has a bandwidth ($\Delta\lambda$) of approximately 30 nm. For the third subassembly, the light source 16 is preferably a superluminescent diode that generates a light beam 22 (dotted line) having a wavelength of approximately 800 nm. In the case of the light beam 22, however, the bandwidth ($\Delta\lambda$) needs to be very broad and will, preferably, be in a range around 150-200 nm. It will be appreciated that the light source 16 for system 10 may be a femtosecond laser.

Figure 2:
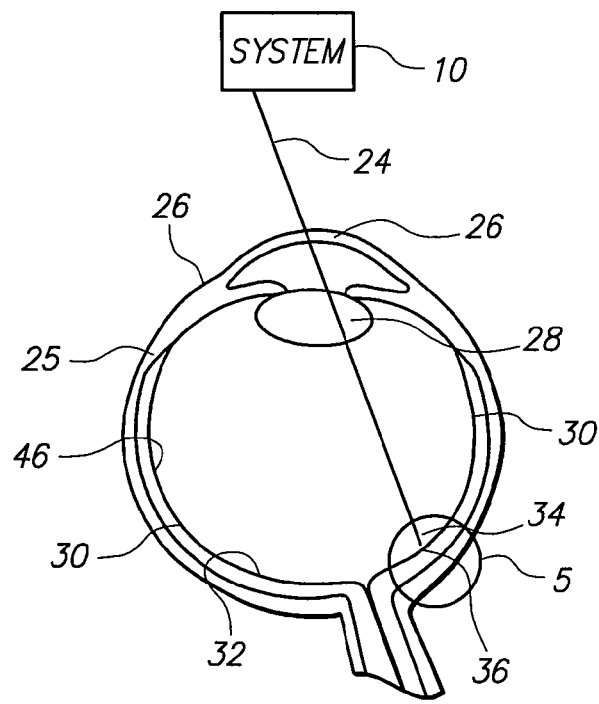
FIG. 2 is a cross sectional view of an eye with the system of the present invention operationally positioned relative to the eye.

FIG. 2 indicates that for purposes of the present invention, light from the respective light sources 12, 14 and 16 are directed along the beam path 24 toward an eye 25. Anatomically, the eye 25 is shown with a cornea 26 and a lens 28 that are in the anterior portion of the eye 25. Also, behind these anterior components, the eye 25 is shown with a retina 30 and a fovea 32. In FIG. 2, although the beam path 24 is shown being directed toward a specific location 34 on the retina 30, it is to be appreciated that the beam path 24 can be directed to a plethora of other locations across the retina 30 (including the fovea 32). Accordingly, as envisioned for the present invention, OCT imaging can be accomplished at different locations over substantially all of the retina 30.

Still referring to FIG. 2, it will be seen that light 24 from any of the light sources 12, 14 or 16 can be directed onto a target tissue 36 (e.g. retinal tissue at the location 34). Light 24' will then be backreflected or backscattered from the target tissue 36. Note: as used hereinafter, light that is directed from a light source 12, 14 or 16 toward the eye 25 may simply be designated 24. On the other hand, when this light 24 has been backreflected or backscattered from target tissue 36 it is designated with a prime (i.e. 24'). A similar distinction is made with reference to subassembly light beams 18', 20' and 22'.

Figure 3:
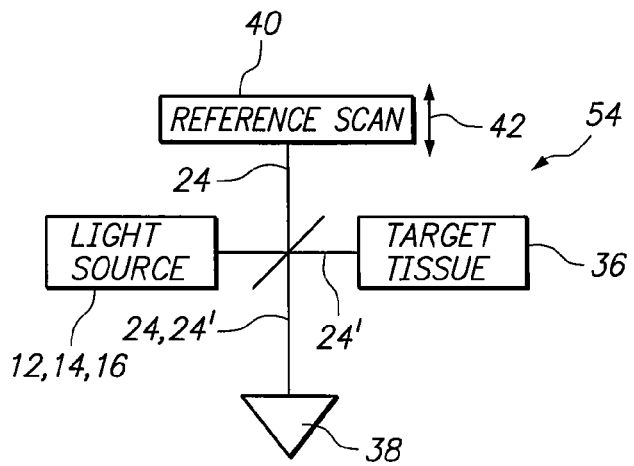
FIG. 3 is a schematic representation of a Michelson interferometer for use in the present invention.

For a general overview of OCT imaging techniques as used for the system 10, reference is initially made to FIG. 3 where a typical Michelson interferometer is schematically shown and is generally designated 54. As shown in FIG. 3, the light 24' that is backreflected or backscattered from the target tissue 36 will be directed to a detector 38. At the detector 38, the light 24' is compared with light 24 from a light source 12, 14 or 16 to identify coherence. Specifically, this is accomplished with a reference scan 40 that can be moved back and forth in the directions indicated by arrows 42 to establish coherence between the light 24 and the backreflected or backscattered light 24'. As will be appreciated by the skilled artisan, coherence allows characteristics of the light 24 to be further analyzed. Of particular importance for the present invention is the coherence that allows for the use of OCT techniques with the second subassembly (i.e. light source 14).

Figure 4:
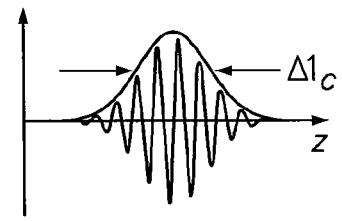
FIG. 4 is a graphic representation of the physical characteristics associated with short coherence length light.

For the present invention, there is a need for good depth resolution ($\Delta z$) in an imaging beam (e.g. light beam 22) of the third subassembly. This then requires light source 16 have a broad bandwidth ($\Delta\lambda$). A consequence of having a broad bandwidth, however, is that the imaging beam 22 will have a short coherence length ($\Delta l_c$). Graphically, this condition is shown in FIG. 4. Mathematically, for a Gaussian spectral distribution, the relationship of depth resolution ($\Delta z$) and coherence length ($\Delta l_c$), with the wavelength ($\lambda$) of light 24 and its bandwidth ($\Delta\lambda$) can be expressed as:

$$\Delta z = \Delta l_c = ((2 \ln 2)/\pi)(\lambda^2/\Delta\lambda)$$

Figure 5:
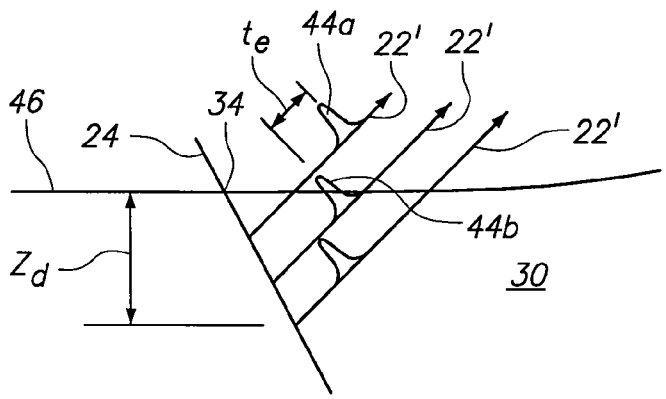
FIG. 5 is an enlarged view of the retina of the eye shown in the area 5 of FIG. 2 showing backscattered light.

In FIG. 5, it is indicated that light 24, with a short coherence length ($\Delta l_c$) but with good depth resolution ($\Delta z$), will create echoes 44 as it passes through tissue. Importantly, the echo time delay ($t_e$) between an echo 44a and a subsequent echo 44b in backscattered light 24' can be measured. With this information, a tomogram of different cell tissue in the retina 30 can be obtained. Specifically, the tomogram can include information from tissue that extends through the retina 30 from its surface 46 down to a predetermined depth ($z_d$).

Figure 6:
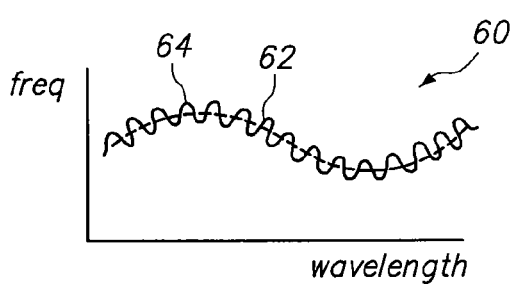
FIG. 6 is a graphic representation of the spectrum in a frequency domain analysis for use in the present invention.

A graphic representation of a spectrum in the frequency domain analysis is depicted in FIG. 6 and is generally designated 60. Specifically, as shown for purposes of disclosure, the spectrum 60 is typical of a response detected by the spectrometer 22 (see FIG. 1), and is illustrated with two components. The low frequency modulation (depicted by dashed line 62) is due to a retinal membrane having a shallow depth extent. On the other hand, the higher frequency component (depicted by solid line 64) is indicative of a retinal membrane having a greater thickness.

Operation

In overview, the first subassembly (i.e. light source 12) is used to measure anterior optical aberrations caused by anterior components of the eye 25, e.g. cornea 26 and lens 28. This is done using backreflected light 24' (i.e. light 18'). The second subassembly (i.e. light source 14) is used to measure phase aberrations caused by retinal tissue between the surface 46 and the predetermined depth $z_d$ in the retina 30. This is done using OCT techniques with backscattered light 24' (i.e. light 20'). Finally, the actual imaging of tissue cells in the retina 30 is done by the third subassembly using backscattered light 24' (i.e. light 22'). Importantly, the refractive errors (aberrations) detected by the first and second subassemblies are removed from the imaging light beam 22' before imaging is accomplished.

In the operation of the system 10 of the present invention, the light source 12 (i.e. first subassembly) is activated to generate and direct the light beam 18 along beam path 24 into the eye 25. Specifically, the purpose here is to then receive backreflected light 18' from the retina 30 with which anterior optical aberrations introduced by the cornea 26 and lens 28 can be measured. Preferably, due to its relatively high reflectance, the fovea 32 of retina 30 will be used. As shown in FIG. 1 this backreflected light 18' is evaluated by a wavefront sensor 48 and passed to a computer 50 for measurement. Specifically, this measurement will define the anterior optical aberrations that are introduced into the light 24 by the anterior components of the eye 25 (i.e. cornea 26 and lens 28). For system 10, the wavefront sensor 48 will preferably be a Hartmann-Shack sensor, of a type well known in the pertinent art. After, the backreflected light 18' has been measured, these measurements are used in the system 10 to program an active mirror 52. More specifically, the active mirror 52 is programmed to remove the anterior optical aberrations measured in light beam 18' from the imaging light beam 22.

Still referring to FIG. 1, after anterior optical aberrations have been measured by the first subassembly (i.e. light source 12), and appropriate programming of the active mirror 52 has been accomplished, the second subassembly (i.e. light source 14) is activated. In this instance, the light beam 20 is directed toward the retinal tissue cells at location 34 that are to be imaged. Backscattered light 20' from the retina 30 at location 34 is then passed to the interferometer 54 for wavelength analysis, and for identifying coherence. From the interferometer 54 the light 20' is passed to the wavefront sensor 48. Again, as was done with the backreflected light 18' in the first subassembly, the backscattered light 20' in this second subassembly is measured by the wavefront sensor 48 and computer 50. Specifically, these measurements are indications of the phase aberrations introduced into the light 20' as it passes from the surface 46 of retina 30 to a depth in the retina 30 (e.g. predetermined depth "$z_d$"). Also, like the measurements from backreflected light 18', these measurements are used to program the active mirror 52, and thereby subsequently remove phase aberrations from the imaging light beam 22.

With the active mirror 52 appropriately programmed to remove anterior optical aberrations (first subassembly) and phase aberrations (second subassembly), the imaging light beam 22 can be directed and focused to the predetermined depth ($z_d$). As shown in FIG. 1, the backscattered light 22' from the retina 30 is then directed by the system 10 to a spectrometer 56 for specific analysis and presentation as an image on an image console 58.

While the particular System and Method for High Resolution Imaging of Cellular Detail in the Retina as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for imaging a tissue cell at a predetermined depth in the retina of an eye, with compensation for refractive errors, the system comprising:
   a first light source for directing a first light beam into the eye;
   a means for measuring anterior optical aberrations introduced by components of the eye as the first light beam is directed through the eye and onto the retina;
   a second light source for directing a second light beam through retinal tissue to the predetermined depth, wherein the anterior optical aberrations have been substantially removed from the second light beam;
   a means for using the second light beam to measure phase aberrations introduced by the retinal tissue; and
   a third light source for directing a third light beam to the tissue cell to produce an image of the tissue cell, wherein the anterior optical aberrations and the phase aberrations have been substantially removed from the third light beam.

2. A system as recited in claim 1 wherein the anterior optical aberrations are determined by directing the first light beam onto the fovea of the retina and evaluating a specular reflection from the fovea.

3. A system as recited in claim 2 wherein the first light source generates the first light beam having a wavelength in a range of 478-498 nm.

4. A system as recited in claim 1 wherein the second light beam has a wavelength in a range of 790-810 nm and a bandwidth in a range of 28-32 nm, for use in a time domain OCT technique with a resolution in a range of 15-20 microns, to measure the phase aberrations introduced by retinal tissue between the surface of the retina and the predetermined depth.

5. A system as recited in claim 4 wherein the second light source is a superluminescent diode and the system further comprises:
   an interferometer to select backscattered light from depths in the retina; and
   a wavefront sensor for analyzing the back scattered light to determine the phase aberrations.

6. A system as recited in claim 1 wherein the third light beam has a wavelength in a range of 790-810 nm and a bandwidth in a range of 190-210 nm, for use in a Fourier domain OCT technique with ultra-high resolution of less than 5 microns, to image the tissue cell.

7. A system as recited in claim 6 wherein the third light source is a superluminescent diode.

8. A system as recited in claim 1 further comprising:
a first wavefront sensor for detecting the anterior optical aberrations in the first light beam; and
a first active mirror positioned on a beam path of the second light beam and programmed with the anterior optical aberrations from the first wavefront sensor to remove the anterior optical aberrations from the second light beam.

9. A system as recited in claim 8 further comprising:
a second wavefront sensor for detecting the phase aberrations in the second light beam; and
a second active mirror positioned on a beam path of the third light beam and programmed with the phase aberrations from the second wavefront sensor to remove the phase aberrations from the third light beam.

10. A system as recited in claim 9 wherein the first and second wavefront sensors are a same Hartmann-Shack sensor, and the first and second active mirrors are a same active mirror.

11. A system for imaging a tissue cell at a predetermined depth in the retina of an eye, with compensation for refractive errors, the system comprising:
a first optical means having a first light source for generating and directing a first light beam into the eye, for measuring anterior optical aberrations caused by optical components of an eye;
a second optical means having a second light source for generating and directing a second light beam onto the retina, for measuring phase aberrations caused by retinal tissue in the eye, wherein the retinal tissue extends from the surface of the retina to the predetermined depth; and
a third optical means having a third light source for generating an imaging light beam, with means for removing the anterior optical aberrations and the phase aberrations from the imaging light beam to image the tissue cell at the predetermined depth in the retina.

12. A system as recited in claim 11 wherein the first light beam has a wavelength in a range of 478-498 nm and wherein the first optical means further comprises:
a first wavefront sensor for use in measuring the anterior optical aberrations in the first light beam; and
a first active mirror programmed with the anterior optical aberrations from the first wavefront sensor.

13. A system as recited in claim 12 wherein the second light beam has a wavelength in a range of 790-810 nm and a bandwidth in a range of 28-32 nm, for use in a time domain OCT technique with a resolution in a range of 15-20 microns, to measure the phase aberrations introduced by retinal tissue between the surface of the retina and the predetermined depth, and wherein the second optical means comprises:
a second wavefront sensor for use in measuring the phase aberrations in the second light beam; and
a second active mirror programmed with the phase aberrations from the second wavefront sensor.

14. A system as recited in claim 13 wherein the third optical means includes at least one active mirror.

15. A system as recited in claim 11 wherein the imaging light beam has a wavelength in a range of 790-810 nm and a bandwidth in a range of 190-210 nm, for use in a Fourier domain OCT technique with ultra-high resolution of less than 5 microns, to image the tissue cell.

16. A system as recited in claim 15 wherein the light source is a superluminescent diode.

17. A method for imaging a tissue cell at a predetermined depth in the retina of an eye, with compensation for refractive errors, which comprises the steps of:
measuring with a first light beam anterior optical aberrations caused by optical components of an eye;
measuring with a second light beam phase aberrations caused by retinal tissue in the eye, wherein the retinal tissue extends from the surface of the retina to the predetermined depth;
generating a third light beam for imaging; and
removing the anterior optical aberrations and the phase aberrations from the third light beam to image the tissue cell at the predetermined depth in the retina.

18. A method as recited in claim 17 wherein the step for measuring anterior optical aberrations comprises the steps of:
generating the first light beam, wherein the first light beam has a wavelength in a range of 478-498 nm;
directing the first light beam into the eye;
detecting the anterior optical aberrations in the first light beam; and
programming an active mirror with the anterior optical aberrations to remove the anterior optical aberrations from the imaging light beam.

19. A method as recited in claim 18 wherein the step for measuring phase aberrations comprises the steps of:
generating the second light beam, wherein the second light beam has a wavelength in a range of 790-810 nm and a bandwidth in a range of 28-32 nm, for use in a time domain OCT technique with a resolution in a range of 15-20 microns;
directing a second light beam onto the retina;
detecting the phase aberrations in the second light beam; and
programming the active mirror with the phase aberrations to remove phase aberrations from the imaging light beam.

20. A method as recited in claim 17 wherein the third light beam has a wavelength in a range of 790-810 nm and a bandwidth in a range of 190-210 nm, for use in a Fourier domain OCT technique with ultra-high resolution of less than 5 microns.

* * * * *